United States Patent [19]
Grenouillet et al.

[11] Patent Number: 4,889,949
[45] Date of Patent: Dec. 26, 1989

[54] CATALYTIC (CO)DIMERIZATION OF ALKYL ACRYLATES

[75] Inventors: Pierre Grenouillet, Fontaines Sur Saone; Denis Neibecker, Neuves-Maisons; Igor Tkatchenko, Caluire, all of France

[73] Assignee: Rhone-Poulenc Chimie, Courbevoie, France

[21] Appl. No.: 212,678

[22] Filed: Jun. 28, 1988

Related U.S. Application Data

[62] Division of Ser. No. 28,569, Mar. 20, 1987, Pat. No. 4,786,623.

[30] Foreign Application Priority Data

Mar. 27, 1986 [FR] France ................................ 86 04644

[51] Int. Cl.$^4$ ............................................ C07C 67/343
[52] U.S. Cl. .................... 560/202; 502/155; 502/154; 502/162; 502/164; 562/598
[58] Field of Search ................ 560/202; 502/155, 162, 502/164, 154

[56] References Cited

U.S. PATENT DOCUMENTS

| 4,243,829 | 1/1981 | Pittman et al. ................ 502/162 X |
| 4,451,665 | 5/1984 | Nugent ................ 560/202 |
| 4,501,822 | 2/1985 | Foley ................ 502/162 |
| 4,519,954 | 5/1985 | Burrington et al. ............ 502/162 X |
| 4,594,447 | 6/1986 | Wilke et al. ................ 560/202 |
| 4,634,793 | 1/1987 | Drent ................ 560/202 X |

Primary Examiner—Werren B. Lone
Assistant Examiner—Vera C. Clarke
Attorney, Agent, or Firm—Burns, Doane, Swecker & Mathis

[57] ABSTRACT

The alkyl acrylates, e.g., methyl or ethyl acrylate, are improvedly dimerized, or codimerized with a conjugated diene, by contacting same with a catalytically effective amount of (a) at least one palladium source, (b) at least one organophosphorus(III) compound, and (c) at least one hydracid HY, the anion Y$^-$ of which does not coordinate with palladium ions.

13 Claims, No Drawings

CATALYTIC (CO)DIMERIZATION OF ALKYL ACRYLATES

This application is a divisional of application Ser. No. 028,569, filed Mar. 20, 1987, now U.S. Pat. No. 4,786,623.

BACKGROUND OF THE INVENTION

1. Field of the Invention

The present invention relates to the catalytic (co)dimerization of an alkyl acrylate in the presence of certain palladium complexes, and, more especially, to the catalytic dimerization of alkyl esters of acrylic acid to produce alkyl diesters of dihydromuconic acid.

2. Description of the Prior Art

Certain palladium derivatives are known to this art to catalyze the dimerization of alkyl acrylates. Thus, bis(benzonitrile)palladium(II) chloride, $(C_6H_5CN)_2 PdCl_2$, has been used for the dimerization of methyl acrylate; Barlow et al, *J. Organometal. Chem.*, 21, 215 (1970). Nevertheless, this system is not very efficient because, as reported, a conversion of only 67% for a selectivity to dimers of 93%, 90% of which was to straight-chain dimer, was attained over 23 hours at 113° C. The reaction rate was improved by adding silver tetrafluoroborate, $AgBF_4$, to the reaction mixture; Oehme et al, *Tetrahedron Letters*, 4, 343 (1979). This reaction rate was also improved by adding p-benzoquinone, according to Pracejus et al, *Z. Chem.*, 20, 24 (1980).

The efficiency of cationic complexes of palladium having the formula $Pd(NCMe)_4(BF_4)_2$, especially in the presence of anhydrous $LiBF_4$ is also known to this art, because at 40° C. in 30 hours, a 93% yield of methyl acrylate dimers is attained after distillation, the selectivity to the $\Delta^2$-trans isomer being on the order of 93–96%. See Nugent et al, *J. Oro. Chem.*, 48, 5364–5366 (1983).

Moreover, the codimerization of 1,3-butadiene and methyl acrylate to form methyl heptadienoates, catalyzed by a mixture of palladium chloride of the π-allyl type, a phosphine and a silver salt is also known to the art. Compare French Pat. No. 2,079,319.

The catalysis of the dimerization of an alkyl acrylate, or of the codimerization of such types of compounds with a conjugated diene compound by means of a cationic allyl complex of palladium, modified by the addition of a phosphine, has also been proposed to the art (French Pat. No. 2,524,341), the subject complexes being prepared from the palladium compound and dibenzylidene acetone and an allyloxytris(dimethylamino)phosphonium salt and 1,5-cyclooctadiene.

In capsule summary, all of the foregoing reactions, when using the readily available palladium complexes, such as:

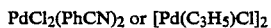

are typically slow and/or not very selective. Any improvement in the activity and/or selectivity of these reactions is accompanied by an increase in the complexity of the palladium compounds, and, therefore, in the cost of preparing them and by increased difficulties in the use thereof, caused, in particular, by their instability.

Thus, serious need exists for dimerization catalytic systems which are both more efficient and more economical than those heretofore proposed to this art.

SUMMARY OF THE INVENTION

Accordingly, a major object of the present invention is the provision of an improved process for the catalytic (co)dimerization of a lower alkyl acrylate by contacting a lower alkyl acrylate and, where appropriate, a conjugated diene compound, with a catalytic system which comprises palladium or a palladium compound, at a temperature of from 50° to 250° C., said catalytic system comprising:

(a) at least one nonhalogenated palladium compound;
(b) at least one phosphorus(III) compound having the general formula (I):

in which $R_1$, $R_2$ and $R_3$ are independently an alkyl, cycloalkyl, aryl, alkoxy, cycloalkoxy or aryloxy radical, with the proviso that one of said radicals $R_1$, $R_2$ or $R_3$ can be a monovalent radical having the general formula (II):

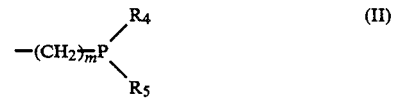

in which m is an integer ranging from 1 to 4, inclusive, $R_4$ and $R_5$ are independently an alkyl, cycloalkyl, aryl, alkoxy, cycloalkoxy or aryloxy radical; and (c) at least one hydracid HY, the anion $Y^-$ of which does not coordinate with palladium ions.

This invention also features the aforesaid catalytic compositions, per se, useful for carrying out the topic dimerization reactions.

DETAILED DESCRIPTION OF THE PREFERRED EMBODIMENTS OF THE INVENTION

More particularly according to the present invention, one starting material is advantageously a lower alkyl acrylate, i.e., the alkyl moiety of which contains from 1 to 8 carbon atoms. The size of the alkyl group is not critical and methyl acrylate or ethyl acrylate are more preferred because of their greater availability. The alkyl group may contain substituents which do not interfere with the dimerization reaction.

Where appropriate, a second starting material is used, namely, a conjugated diene typically having the formula:

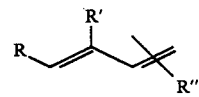

in which R, R' and R'' are each a hydrogen or chlorine atom, or an alkyl radical containing not more than 4 carbon atoms.

Exemplary of such dienes, butadiene, isoprene, cis- and trans-piperylenes, 2,3-dimethylbutadiene and chloroprene are representative.

Commercial-grade products which are not necessarily pure may, of course, be used as starting materials.

In the codimerization process, the two starting materials are used in substantially equimolecular proportions.

The catalytic system according to the invention is formed from at least one nonhalogenated palladium compound. This palladium source, which is the precursor for the catalytically active entity, may be selected from among the various nonhalogenated forms of palladium(O) or palladium(II). Among the palladium(II) forms suitable for implementing the process according to the invention, exemplary are: organic acid salts, such as palladium(II) acetate, palladium(II) formate, palladium(II) propionate, palladium(II) octanoate and palladium(II) ethylhexanoate; inorganic acid salts, such as palladium(II) nitrate; and palladium(II) π-allyl complexes, such as (π-allyl)palladium diacetate and palladium(II) acetylacetonate.

The use of palladium(II) acetate or of palladium(II) acetylacetonate is particularly advantageous because of the greater availability thereof.

Exemplary of the palladium(O) sources which are suitable according to the present invention, representative are: palladium black, palladium deposited onto a support, such as active charcoal or silica gel, and complexes of palladium and a trialkyl- or triaryl-phosphine, such as tetrakis(triphenylphosphine)palladium.

The compounds of palladium(O) and dibenzylideneacetone having the following general formula (III) are particularly suitable according to this invention:

$$Pd_x(dba)_y \quad (III)$$

in which x is equal to 1 or 2; dba is a dibenzylideneacetone coordinate; and y is equal to 2 or 3, with the proviso that y is necessarily equal to 3 when x equals 2.

These compounds are easily prepared. They may readily be produced by the reduction of palladium chloride in the presence of dibenzylideneacetone (dba) according to any one of the procedures described by Y. Ishii et al, Chem. Comm., p. 1065 (1970).

Any of the complexes Pd(dba)$_2$, Pd$_2$(dba)$_3$ and Pd(dba)$_3$, or mixture thereof, may be used.

The concentration of palladium in the reaction medium may vary over wide limits. An amount of at least 0.1 millimole per mole of acrylate appears to be necessary to provide an adequate conversion rate. No advantage is observed in exceeding an amount of 3 millimoles per mole of acrylate. An amount ranging from 0.2 to 1.5 millimoles per mole of acrylate has been determined to be an acceptable compromise between the cost and the efficiency of the catalyst system.

The catalytic system according to the invention is thus comprised of at least one phosphorus(III) compound having the general formula (I):

in which R$_1$, R$_2$ and R$_3$ are as defined above, again with the proviso that one of the radicals R$_1$ to R$_3$ can be a monovalent radical having the general formula (II):

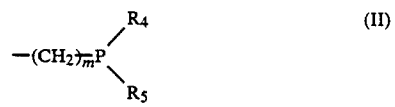

in which m, R$_4$ and R$_5$ are as defined above.

More specifically, R$_1$, R$_2$ and R$_3$, which may be identical or different, are each:
(i) an alkyl radical containing not more than 8 carbon atoms, such as methyl, ethyl, propyl, isopropyl, butyl, tert-butyl and n-octyl radicals;
(ii) a cycloalkyl radical containing from 5 to 7 carbon atoms, such as a cyclohexyl or cycloheptyl radical;
(iii) an aryl radical containing from 6 to 12 carbon atoms, such as phenyl, p-toluyl, biphenylyl and naphthyl radicals;
(iv) an alkoxy radical containing not more than 8 carbon atoms, such as methoxy and ethoxy radicals; and
(v) an aryloxy radical containing from 6 to 12 carbon atoms, such as a phenoxy radical.

Exemplary of the phosphines or phosphites of the formula (I) above, representative are: tributylphosphine, tricyclohexylphosphine, triethylphosphite, dimethylphenylphosphine and triphenylphosphite.

Exemplary of the diphosphines of formula (II), representative are:
bis(dimethylphosphino)methane,
bis(diphenylphosphino)methane,
bis(diphenylphosphino)ethane,
bis(diphenylphosphino)propane,
bis(diphenylphosphino)butane, and
bis(dicyclohexylphosphino)ethane.

Phosphines containing at least one alkyl or cycloalkyl radical, and more particularly trialkylphosphines, are the preferred.

Tributylphosphine is advantageously used. The amount of the phosphorus(III) compound is typically such that the molar ratio P/Pd ranges from 1 to 15 and, preferably from 1 to 3.

The catalytic system according to the present invention is formed from the two types of compounds (Pd, P) mentioned above, to which a hydracid HY is added, the associated anion Y$^-$ of which does not coordinate with palladium ions. The hydracids are typically strong acids, the anion Y$^-$ of which is selected from among the following anions: $C_nF_{2n+1}CO^-_2$, $C_nF_{2n+1}SO^-_3$, $\frac{1}{2}SO^=_4$, $ClO^-_4$, $PF^-_6$, $SbF^-_6$, $BF^-_{4\Delta}$ and $\frac{1}{2}SiF^=_6$, with n being an integer ranging from 1 to 4, inclusive.

Tetrafluoroboric acid is more preferred for preparation of the subject catalytic system.

The ratio H$^+$/Pd typically ranges from 1 to 30, and preferably from 1 to 10. This ratio is related to the molar ratio P/Pd; good results are obtained using a ratio H$^+$/P on the order of approximately 2 to 5.

The preparation of the catalytic system is carried out by the successive addition, where appropriate in a solvent medium, of the phosphorus(III) compound and the hydracid to the palladium source. In another embodiment of the invention, such preparation includes the prior synthesis of a hydrogenophosphonium salt of the formula:

$$[HPR_1R_2R_3]^+Y^-$$

by adding, in a solvent medium where appropriate, the hydracid to the phosphorus(III) compound, when the latter is sufficiently basic, e.g., tributylphosphine, tricyclohexylphosphine and dimethylphenylphosphine. The different amounts of Pd, P and H+ mentioned above are applicable.

The reaction solvent may be the (or one of the) substrate(s) employed in the catalytic reaction. Solvents which do not interfere with the catalytic reaction itself are also suitable. Saturated or aromatic hydrocarbons, aliphatic and aromatic halides, esters and ethers are representative examples of such solvents.

The preparation of the catalytic system is carried out at a temperature of from ambient (approximately 20° C.) to approximately 100° C. a temperature in the range of from 40° to 100° C. is preferably used.

The (co)dimerization reaction is typically carried out at a temperature of from 50° to 250° C., preferably in the vicinity of 70° to 200° C., for a period of time of from 10 minutes to 72 hours, and preferably from 30 minutes to 20 hours.

The reaction products are advantageously recovered by distillation, after neutralizing the reaction medium when an excess of hydracid is employed, and, where appropriate, after a first distillation to remove a third solvent, when required.

(i) the equivalent of 0.2 millimole (mmol) of palladium, of a 1:3 mixture of the complexes Pd(dba)$_2$ and Pd$_2$(dba)$_3$;
(ii) degassed, commercial-grade methyl acrylate;
(iii) tributylphosphine (PBu$_3$) redistilled under argon; and
(iv) tetrafluoroboric acid dissolved in diethyl ether, the titer of which was determined beforehand.

The tube was then closed and the contents were heated at a temperature of 80° C. for the desired period of time, under stirring. It was then cooled to ambient temperature and the reaction medium was then neutralized by adding 0.5 g of sodium bicarbonate. The contents were distilled under reduced pressure (3 torr) and the liquid fraction was collected.

The distillate thereby obtained was then analyzed by gas chromatography, using methyl malonate as the internal standard, with a column: 2 m × ⅛" Carbowax 20 M (10%) on Chromosorb PAW 60-80. The injector temperature was 250° C., oven temperature 150° C., flame ionization detector temperature 250° C., and nitrogen (25 ml/mn) was used as the vector gas.

The specific conditions and the results obtained are reported in Table I below:

TABLE 1

Dimerization Of Methyl Acrylate - Effect Of The Proportions Of Pd/P/H+ And Time (Reaction Temperature: 80° C.):

| Example Number | [Pd(O)] mmol | [PBu$_3$] mmol | [HEF$_4$] mmol | Methyl acrylate mmol | Time hr | Conversion % | % SELECTIVITIES | | | |
|---|---|---|---|---|---|---|---|---|---|---|
| | | | | | | | DELTA-2 | DELTA-3 | ME-2G | Others |
| 1 | 0.2 | 0.2 | 0.2 | 157 | 20 | 4 | 94 | 1 | 1 | 4 |
| 2 | 0.2 | 0.2 | 0.4 | 152 | 20 | 39 | 95 | tr. | 1.5 | 3 |
| 3 | 0.2 | 0.2 | 0.6 | 157 | 20 | 53 | 95 | tr. | 1 | 4 |
| 4 | 0.2 | 0.2 | 0.8 | 147 | 20 | 40 | 94 | tr. | 1.5 | 4 |
| 5 | 0.2 | 0.2 | 1 | 153 | 20 | 21 | 95 | tr. | 2 | 3 |
| 6 | 0.2 | 0.4 | 0.4 | 156 | 20 | 12 | 94 | tr. | 1.5 | 4.5 |
| 7 | 0.2 | 0.4 | 0.6 | 152 | 20 | 55 | 95 | tr. | 1 | 4 |
| 8 | 0.2 | 0.4 | 0.8 | 154 | 20 | 87 | 96 | tr. | 1 | 3 |
| 9 | 0.2 | 0.4 | 1 | 149 | 20 | 87 | 96 | tr. | 1 | 4 |
| 10 | 0.2 | 0.6 | 0.8 | 136 | 20 | 55 | 95 | tr. | 2 | 3 |
| 11 | 0.2 | 0.6 | 1 | 145 | 20 | 53 | 95 | 1 | 1 | 3 |
| 12 | 0.2 | 0.4 | 0.8 | 153 | 5 | 64 | 96 | tr. | 1 | 3 |
| 13 | 0 | 0.2 | 0.2 | 150 | 20 | 95 | | | | polym. |
| 14 | 0.2 | 0 | 0.2 | 136 | 20 | 0 | | | | — |
| 15 | 0.2 | 0 | 0.4 | 141 | 20 | 0 | | | | — |
| 16 | 0.2 | 0.2 | 0 | 140 | 20 | 0 | | | | — |
| 17 | 0 | 0 | 0.2 | 150 | 20 | 0 | | | | — |

The process is particularly well adapted for the dimerization of alkyl acrylates, especially methyl or ethyl acrylate. The diesters thereby obtained are useful intermediates in the preparation of adipic acid.

In order to further illustrate the present invention and the advantages thereof, the following specific examples are given, it being understood that same are intended only as illustrative and in nowise limitative.

In said examples to follow, the following conventions are used:

"DELTA-2" denotes Δ$^2$-methyl dihydromuconate;
"DELTA 3" denotes Δ$^3$-methyl dihydromuconate;
"ME-2G" denotes methyl 2-methyleneglutarate;
"polym." denotes polymers; and
"tr." denotes traces.

EXAMPLES 1 TO 17

These examples illustrate the dimerization of methyl acrylate according to the following general procedure:

The following ingredients were successively introduced into a Schlenk tube equipped with a bar magnet and purged with argon:

In Example 13 (not according to the invention), it was shown that only polymers were formed in the absence of palladium.

In Example 14 (not according to the invention), it was shown that no conversion of acrylate was observed in the absence of the phosphorus(III) compound.

In Example 15 (not according to the invention), it was shown that no conversion of acrylate was observed in the absence of the phosphorus(III) compound and in the presence of an increased amount of hydracid.

In Example 16 (not according to the invention), it was shown that no conversion of acrylate was observed in the absence of hydracid.

In Example 17 (not according to the invention), it was shown that the presence of the hydracid alone was insufficient to ensure any conversion of acrylate.

EXAMPLES 18 AND 19

These examples included the preforming of the salt [HPBu$_3$]BF$_4$.

The following ingredients were successively introduced into a Schlenk tube equipped with a bar magnet and purged with argon:
(i) the equivalent of 0.2 millimole of palladium, of the mixture of complexes described above;
(ii) degassed, commercial-grade methyl acrylate; and
(iii) hydrogenotributylphosphonium tetrafluoroborate formed by the reaction of equivalent amounts of tributylphosphine and tetrafluoroboric acid dissolved in diethyl ether and, where appropriate, tetrafluoroboric acid dissolved in diethyl ether.

The Schlenk tube was closed and the contents were then stirred at 80° C. for 20 hours. The treatment of the reaction mixtures according to the procedure described previously gave the results reported in Table II below:

TABLE II

| | | | | | | | | |
|---|---|---|---|---|---|---|---|---|
| Dimerization Of Methyl Acrylate/Preforming Of the Salt [HPBu₃]BF₄ (Reaction at 80° C., in 20 hr) | | | | | | | | |
| Example Number | [Pd(O)] mmol | [PBu₃] mmol | [HEF₄] mmol | Methyl acrylate mmol | Conversion % | % SELECTIVITIES | | |
| | | | | | | DELTA-2 | DELTA-3 | ME-2G | Others |
| 18 | 0.2 | 0.2 | 0.2 | 156 | 23 | 96 | tr. | 1 | 3 |
| 19 | 0.2 | 0.4 | 0 | 163 | 12 | 95 | tr. | 1.5 | 3.5 |

EXAMPLE 20

This example illustrates the effect of the concentration of the catalyst precursor.

The following ingredients were introduced successively into a Schlenk tube equipped with a bar magnet and purged with argon:
(i) the equivalent of 0.1 milligram-atom of palladium, of the mixture of complexes described above;
(ii) degassed, commercial-grade methyl acrylate (13.8 ml, which is 153 mmol);
(iii) tributylphosphine (PBu₃) (40 mg, which is 0.2 mmol); and
(iv) a 9.3 N solution of tetrafluoroboric acid in diethyl ether (0.05 ml, which is 0.4 mmol).

The Schlenk tube was closed and the contents were shaken for 20 hours at 80° C. The treatment of the reaction mixture according to the procedure described previously gave a 41% conversion of methyl acrylate. The selectivities observed were as follows:
(a) $\Delta^2$-Methyl dihydromuconate: greater than 95%;
(b) Methyl 2-methyleneglutarate: 1%;
(c) $\Delta^3$-Methyl dihydromuconate: traces; and
(d) Unidentified dimers: 3%.

EXAMPLE 21

This example illustrates the codimerization of methyl acrylate and butadiene.

The following ingredients were introduced successively into a glass-lined 100 ml stainless steel autoclave equipped with a jacket and a bar magnet, and purged beforehand with argon:
(i) the equivalent of 0.25 millimole of palladium, of the mixture of complexes described above;
(ii) degassed, commercial-grade methyl acrylate (13.5 ml, which is 150 mmol);
(iii) a 9.3 N solution of tetrafluoroboric acid in diethyl ether (0.125 ml, which is 1 mmol).

The autoclave was closed, cooled and then pressurized with butadiene (8.1 g, which is 150 mmol). The autoclave was then connected to a thermostat containing circulating oil maintained at 80° C. an stirred for 5 hours. The autoclave was cooled and the residual butadiene was collected in a trap maintained at −30° C. The reaction mixture was then treated as before, and then analyzed by gas chromatography. The conversion of methyl acrylate was 89%; the conversion of butadiene was 90%. The selectivities observed were as follows:
(a) Methyl hepta-2, trans-5, trans-dieonoate: 68%;
(b) Methyl 3-cyclohexenecarboxylatic: 2%;
(c) Other unidentified codimers: 10%;
(d) Octatrienes: 3%; and
(e) Heavy products: 17%.

EXAMPLE 22

This example illustrates the codimerization of methyl acrylate and isoprene.

Under the same conditions as in Example 21, a mixture of methyl acrylate (14.3 ml, which is 159 mmol) and isoprene (13.5 ml, which is 135 mmol) was stirred for 20 hours at 80° C.

The conversion of methyl acrylate was 90%; the conversion of isoprene was 100%.

The selectivities determined by gas chromatography were:
(a) Methyl 5-methyl-hepta-2, trans-5, transdienoate: 60%;
(b) Methyl 5-methyl-hepta-2, trans-4, transdienoate: 13%;
(c) $\Delta^2$-Methyl dihydromuconate: 8%; and
(d) Heavy products: 19%.

EXAMPLE 23

This example illustrates the use of palladium acetate in the dimerization of methyl acrylate.

The following ingredients were introduced successively into a Schlenk tube equipped with a bar magnet, and purged with argon:
(i) palladium acetate (source: Johnson-Matthey; 22.5 mg; 0.1 mmol);
(ii) degassed, commercial-grade methyl acrylate (13.8 ml; 153 mmol);
(iii) tributylphosphine (60 mg; 0.3 mmol); and
(iv) a 9.3 N solution of tetrafluoroboric acid in diethyl ether (0.075 ml; 0.6 mmol).

The Schlenk tube was closed, and then stirred for 5 hours at 80° C. The treatment of the reaction mixture according to the procedure described previously gave a 52% conversion of methyl acrylate (rotation speed: 76 h⁻¹). The selectivity to $\Delta^2$-methyl dihydromuconate was greater than 95%.

EXAMPLE 24

This example illustrates the use of palladium acetylacetonate in the dimerization of methyl acrylate.

The following ingredients were introduced successively into a Schlenk tube equipped with a bar magnet, and purged with argon:

(i) palladium acetylacetonate (prepared according to published German Pat. Application No. 2,904,235; 30.5 mg; 0.1 mmol);
(ii) degassed, commercial-grade methyl acrylate (14 ml; 155 mmol);
(iii) tributylphosphine (40 mg; 0.2 mmol); and
(iv) a 9.3 N solution of tetrafluoroboric acid in diethyl ether (0.125 ml; 1.0 mmol).

The Schlenk tube was closed, and then stirred for 5 hours at 80° C. The treatment of the reaction mixture according to the procedure described above gave a 67% conversion of methyl acrylate (rotation speed: 88 $h^{-1}$). The selectivity to $\Delta^2$-methyl dihydromuconate was greater than 95%.

EXAMPLE 25

This example illustrates the dimerization of methyl acrylate according to another procedure:

A stainless steel autoclave (Z 8 CNDT 1712), purged beforehand with argon, was charged with:
(i) methyl acrylate : 13.2 g (154 mmol);
(ii) Pd(dba)$_2$ : 0.2 mmol;
(iii) PBu$_3$ : 0.4 mmol: and
(iv) HBF$_4$ : 0.8 mmol.

The autoclave was sealed air-tight and then placed in an oven, agitated by shaking; the temperature was adjusted to 80° C., the reaction period was 20 hours. The autoclave was then cooled, and a clear orange reaction mass was obtained No palladium metal was observed in the reaction mass. Analysis showed that it consisted of methyl hexenedioates (49% yield) and methyl 2-methylenepentanedioate (6.4%).

EXAMPLE 26

The reaction was carried out in the same manner as in Example 25, except that the reaction temperature was 120° C. and the reaction time was 3 hours. A clear orange reaction mass was obtained; the formation of palladium metal was not observed. The yield of methyl hexenedioates was 58%.

EXAMPLE 27

The reaction was carried out as in Example 25, except that palladium was introduced in the form of Pd(acac)$_2$ (acac: acetylacetonate), the temperature was 100° C. and the reaction time was 3 hours. A clear yellow reaction mass was obtained. No formation of palladium metal was observed The yield of methyl hexenedioates was 49%.

EXAMPLES 28 TO 32

This series of trials illustrates the effect of temperature; the experiments were carried out according to the procedure described in Example 25.

A stainless steel autoclave (Z 8 CNDT 1712), purged beforehand with argon, was charged with:
(i) Pd(acac)$_2$ : 0.4 mmol;
(ii) methyl acrylate : 161 mmol;
(iii) a solution of PBu$_3$ in methyl acrylate : 0 8 mmol; and
(iv) HBF$_4$.Et$_2$O : 1.6 mmol.

The autoclave was sealed air-tight and then placed in an oven, agitated by shaking, preheated to 215° C.; the temperature was adjusted to 190° C., and the reaction time was 15 minutes The autoclave was then cooled. A clear orange reaction mass was obtained, with a few traces of palladium metal in suspension (this phenomenon was not observed at lower operating temperatures).

Analysis showed that it consisted of methyl hexenedioates (84% yield) and methyl 2-methyleneglutarate (2.6% yield). The specific conditions and the results obtained at different temperatures are reported in Table III below:

TABLE III

| Example Number | T °C. | Reaction period in hr | Yield (%) hexenedioates | Yield (%) ME-2G |
|---|---|---|---|---|
| 28 | 100 | 3 | 37 | 0.6 |
| 29 | 120 | 3 | 67 | 1.4 |
| 30 | 140 | 1 | 95.5 | 2 |
| 31 | 160 | 0.5 | 90 | 2 |
| 32 | 190 | 0.25 | 84 | 2.6 |

EXAMPLE 33

Example 28 was repeated, dividing the palladium charge by two. All other conditions remaining equal, the following yields were respectively obtained:
(a) Methyl hexenedioates 16%;
(b) Methyl 2-methyleneglutarate 0.3%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the dimerization of an alkyl acrylate, or codimerization thereof with a conjugated diene, comprising contacting such acrylate or acrylate/diene with a catalytically effective amount of a catalytic composition of matter, comprising (a) at least one non halogenated palladium source, (b) at least one hydrogenophosphonium salt having the formula:

$[HPR_1R_2R_3]^+Y^-$ and, optionally, (c) a hydracid HY, wherein R$_1$, R$_2$, and R$_3$ are independently an alkyl, cycloalkyl, aryl, alkoxy, cycloalkoxy or aryloxy radical, with the proviso that one of the radicals R$_1$, R$_2$ or R$_3$ can be a monovalent radical having the formula (II):

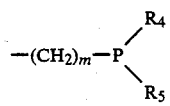

$$-(CH_2)_m-P\begin{matrix}R_4\\R_5\end{matrix}$$

in which m is an integer ranging from 1 to 4 and Y$^-$ is an anion which does not coordinate with palladium ions.

2. A process for the dimerization of an alkyl acrylate, or codimerization thereof with a conjugated diene, comprising contacting such acrylate or acrylate/diene with a catalytically effective amount of a catalytic composition of matter, comprising:
(a) at least one nonhalogenated palladium source;
(b) at least one phosphorus (III) compound having the formula (I):

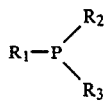

(I)

in which $R_1$, $R_2$ and $R_3$ are independently an alkyl, cycloalkyl, aryl, alkoxy, cycloalkoxy or aryloxy radical, with the proviso that one of the radicals $R_1$, $R_2$ or $R_3$ can be a monovalent radical having the formula (II):

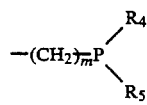

(II)

in which m is an integer ranging from 1 to 4, $R_4$ and $R_4$ are independently an alkyl, cycloalyl, aryl, alkoxy, cycloalkoxy or aryloxy radical; and (c) at least one hydracid HY, the anion $Y^-$ of which does not coordinate with palladium ions.

3. The process as defined by claim 2, wherein said catalytic composition is formulated in a solvent medium.

4. The process as defined by claim 2, wherein $Y^-$, the anion associated with the hydracid (c), comprises $C_nF_{2n+1}CO^-_2$, $C_nF_{2n+1}SO^-_3$, ½ $SO^=_4$, $ClO^-_4$, $PF^-_6$, $SbF^-_6$, $BF^-_4$ or ½ $SiF^=_6$, in which n is an integer of from 1 to 4.

5. The process as defined by claim 2, wherein $Y^-$ is a tetrafluoroborate anion.

6. The process as defined by claim 2, wherein the molar ratio of phosphorus to palladium ranges from 1 to 3.

7. The process as defined by claim 2, wherein the molar ratio of $H^+$ ions to palladium ranges from 1 to 10.

8. The process as defined by claim 2, wherein the phosphorus compound (b) comprises tributylphosphine.

9. The process as defined by claim 1, wherein the hydrogenophosphonium salt (b) comprises hydrogenotributylphosphonium tetrafluoroborate.

10. The process as defined by claim 2, wherein the palladium source (a) comprises palladium(O) of the formula (III):

$$Pd_x(dba)_y \qquad (III)$$

in which x is 1 or 2; dba —
a dibenzylideneacetone coordinate; and y is 2 or 3, with the proviso that y is necessarily 3 when x is 2.

11. The process as defined by claim 2, wherein the palladium source (a) comprises palladium acetate.

12. The process as defined by claim 2, wherein the palladium source (a) comprises palladium acetylacetonate.

13. The process as defined by claim 3, wherein said composition of matter further comprises a solvent selected from the group consisting of alkyl acrylates, conjugated dienes, saturated hydrocarbons, aromatic hydrocarbons, aliphatic halides, aromatic halides, esters, ethers, and mixtures thereof.

* * * * *